(12) United States Patent
Revsbech et al.

(10) Patent No.: US 6,234,004 B1
(45) Date of Patent: May 22, 2001

(54) METHOD FOR MEASUREMENT OF FLOW VELOCITY OR DIFFUSIVITY, MICROSENSOR AND APPLICATION OF SUCH MICROSENSOR

(75) Inventors: Niels Peter Revsbech, Aarhus N; Lars Peter Nielsen, Mårslet; Ole Pedersen, Ringsted; Jens Kristian Gundersen, Viby J., all of (DK)

(73) Assignee: Unisense Aps., Aarhus C (DK)

( * ) Notice: Subject to any disclaimer, the term of this patent is extended or adjusted under 35 U.S.C. 154(b) by 0 days.

(21) Appl. No.: 09/171,047

(22) PCT Filed: Jun. 4, 1997

(86) PCT No.: PCT/DK97/00250

§ 371 Date: Oct. 7, 1998

§ 102(e) Date: Oct. 7, 1998

(87) PCT Pub. No.: WO97/46853

PCT Pub. Date: Dec. 11, 1997

(30) Foreign Application Priority Data

Jun. 6, 1996 (DK) .................................................. 0633/96

(51) Int. Cl.[7] .......................... G01N 13/00; G01N 21/84; G01N 7/00; A61B 5/00
(52) U.S. Cl. .......................... 73/19.1; 73/19.04; 73/19.1; 73/30.03; 73/64.47; 73/61.73; 73/61.47
(58) Field of Search ................................ 73/19.01, 19.04, 73/19.08, 19.1, 23.29, 30.03, 31.05, 40.7, 61.73, 61.47, 61.44, 64.47

(56) References Cited

U.S. PATENT DOCUMENTS

| | | | | |
|---|---|---|---|---|
| 3,221,541 | * | 12/1965 | Osborne | 73/53 |
| 3,401,554 | * | 9/1968 | Bonnet | 73/38 |
| 3,714,829 | * | 2/1973 | Gilbert | 73/398 R |
| 3,738,154 | * | 6/1973 | Henry | 73/19 |
| 3,751,967 | * | 8/1973 | Fick et al. | 73/23 |
| 3,929,003 | * | 12/1975 | Llewellyn | 73/61 R |
| 4,475,556 | * | 10/1984 | Reiff | 128/673 |
| 4,481,808 | * | 11/1984 | Sakata et al. | 73/61.1 R |
| 4,594,884 | * | 6/1986 | Bondi et al. | 73/64.3 |
| 5,013,668 | * | 5/1991 | Fields | 436/168 |
| 5,058,416 | * | 10/1991 | Engelhardt et al. | 73/19.01 |
| 5,138,869 | * | 8/1992 | Tom | 73/31.03 |
| 5,156,041 | * | 10/1992 | Schäper et al. | 73/38 |
| 5,211,055 | * | 5/1993 | Steudle et al. | 73/64.47 |
| 5,288,645 | * | 2/1994 | Toshima et al. | 436/144 |
| 5,587,519 | * | 12/1996 | Ronge et al. | 73/1 G |
| 5,714,678 | * | 2/1998 | Jurcik et al. | 73/31.03 |
| 5,777,203 | * | 7/1998 | Stymne | 73/31.03 |
| 5,827,949 | * | 10/1998 | Ohmi et al. | 73/40 |
| 5,869,749 | * | 2/1999 | Bonne et al. | 73/53.01 |
| 6,089,078 | * | 7/2000 | Chelveder et al. | 73/61.71 |

* cited by examiner

Primary Examiner—Hezron Williams
Assistant Examiner—David J. Wiggins
(74) Attorney, Agent, or Firm—Lee, Mann, Smith, McWilliam, Sweeney & Ohlson

(57) ABSTRACT

The invention relates to a method and a microsensor for measurement of transport coefficients like diffusivity or flow velocity. The microsensor has a reservoir provided with a mouth and a transducer. The transducer has a tip placed in the mouth, which can be provided with a membrane or insert. The reservoir contains one or more gases or one or more liquid-dissolved substances intended for the diffusion through the mouth into an area or field of a medium outside the mouth of the reservoir. The transducer measures the partial pressure of the gas or the concentration of the liquid-dissolved substance in the mouth, whereby transport coefficients of diffusivity or flow velocity are determined. Preferably, the gradient of the partial pressure or the concentration is determined.

16 Claims, 6 Drawing Sheets

METHOD FOR MEASUREMENT OF FLOW VELOCITY OR DIFFUSIVITY, MICROSENSOR AND APPLICATION OF SUCH MICROSENSOR

BACKGROUND OF THE INVENTION

The invention relates to a method for the measurement of diffusivity or flow velocity. The invention also relates to a microsensor for measurement of diffusivity or flow velocity, which microsensor has a reservoir provided with a passage- or transport area and at least one transducer.

Several principles are known for the measurement of flow velocity in fluids. For example the induction principle (Faraday-principle), the skin friction/hot wire principle and the Laser-Doppler-principle. All these principles make use of measuring devices with considerable dimensions. Consequently, the medium where the measurement takes place have to fulfill specific requirements such as sufficient flow and volume.

The U.S. Pat. No. 5,339,694 describes a sensor for measurement of flow in a matrix, more precisely measuring migration of groundwater. The sensor consists of a circular pipe having a liquid permeable diaphragm. Outside the cylinder are transducers for measurement of conductivity. The cylinder contains a saline solution with a conductivity that differs from that of groundwater. When the sensor is placed in a water saturated stratum, salt ions from the cylinder will diffuse through the permeable diaphragm into the stratum with groundwater. A change in the conductivity in an area outside the cylinder is registered by the sensors outside the cylinder, whereby the flow velocity can be determined.

This sensor makes use of a suitable principle for the determination of small flow velocities through bigger volumes of a matrix. However, due to the dimensions of the sensor, it is not possible to use it in smaller volumes such as layer transitions in fluids or in vessels in vegetable or animal tissues, in filters or biofilm.

SUMMARY OF THE INVENTION

Thus, the aim of the present invention is to provide a method and a sensor, which makes use of a better spatial resolution and provides a lower limit of measurement than described in prior art, and which can measure transport coefficients like diffusivity or flow velocity in fluids such as liquids or gasses, or measure in porous matrixes or close to surfaces.

In particular, it is an aim to provide a sensor which can measure in systems where transport of substance or matter takes place as a combination of diffusivity and advection as e.g. close to surfaces and in porous matrixes.

This is achieved with a method where the sensor is placed in an area or volumen of a medium, that a gas or a dissolved substance is diffused into this medium hereby functioning as a tracer material, that the diffusivity or the flow velocity is determined by measuring either the partial pressure of the gas or a concentration of the gas or liquid dissolved substance, whereby the measurement is carried out in the passage- or transport area on the gas or liquid dissolved substance.

Acccording to the invention first microsensor is characterized in that the transducer has a sensoric tip, that is placed in the passage- or transport area, and that the sensoric tip of the transducer is placed in the mouth of the passage- or transport area.

A second embodiment of a microsensor according to the invention is characterized in that the transducer or measuring device is surrounded by the reservoir, which contains a gas or liquid dissolved substance. Preferably, the passage- or transport area is equipped with a permeable membrane or insert, open for diffusion, which is placed in and in sealing contact to the mouth, that the transducer tip is placed in the membrane or insert, and that the reservoir contains a gas or a liquid-dissolved substance intended for diffusion from the reservoir through the membrane or insert to an area or volume outside the mouth.

The transducer can either be placed longitudinally, with its axis parallel with the axis of the passage- or transport area and with the sensoric tip placed in the membrane, or with its axis and sensoric tip mainly vertical to the axis of the passage- or transport area. Especially the longitudinal solution allows a space saving sensor design.

Microsensors with these features can be miniaturized to such a degree that kinetic transport or diffusion coefficients as well as very low flow velocities can be measured. Measurement by means of the inventive microsensor is a true in-situ measurement, and the placing of the microsensor in the medium will not cause substantial changes in transport coefficients. The use of the microsensor does not require a given minimum diffusion coefficient or flow velocity.

The term "fluid" is to be broadly understood as liquids or gasses, and also incorporates gasses with a mist of liquid in the gas or a liquid with a gas contained in the liquid.

The transducer is mainly an electrochemical microsensor, for example a Clark type oxygen micro-electrode, but other types of microsensors like sensors based on optical fibres, so-called optrodes can be used too.

The membrane or insert described in the second embodiment of a microsensor according to the invention is placed at the mouth of a container and is preferably made of silicone.

However, materials that are diffusible or permeable for dissolved non-ionized substances can also be used. The measuring principle for the microsensor can hereby be extended in a way that it comprises not only diffusion of gasses but also diffusion of liquid-dissolved substances like dissolved non-ionized substances from a liquid in the reservoir. The microsensor according to the invention can perform measurements in both gas and liquid media.

The sensor may have a circular mouth at the end of the container, the mouth having a diameter of between 2 $\mu$m and 3 mm, preferably between 2 $\mu$m and 100 $\mu$m. For the measurement of flow velocity 20 $\mu$m is preferred whereas 100 $\mu$m is ideal for measurement of diffusion coefficients. The axial length of the membrane or insert is between 2 $\mu$m and 10 $\mu$m, preferably 20 $\mu$m for measurement of the flow velocity and 100 $\mu$m for measurement of diffusion coefficients.

Using this microsensor it is possible to reach a lower limit for measurement of flow velocity which is less than 5 $\mu$m/s—that is a factor 100 lower than known from prior art. These low values can be measured by the microsensor, where measurement of a partial pressure or a concentration takes place over a very small length inside the sensor. Due to the small dimensions the volume of the medium where the measurement takes place may be reduced considerably.

The sensor is among other uses intended for measurement of flow velocities in fluids with little flow, or in gasses and liquids close to surfaces, but can advantageously be used in other areas, like in human vessels. Furthermore, the microsensor is intended for measurement of molecular or ionic kinetic transport conditions in the form of combined diffusion and flow in porous matrixes in for example biofilm in bioreactors or in animal tissues like brain or liver. Also, measurement in sediments of the sea bed is possible. Hitherto, measurement has mainly been done through use of tracer elements fed into the medium with measurements carried out in the medium itself. With the present invention it is now possible to measure in-situ the transport of miscellaneous substances in vessels, as for example in human tissues.

Consequently, the sensor can be used in many different applications within medical and scientific research as well as within industrial branches like medical and biotechnological industry, where the exchange of a substance between solid surfaces and liquids is an interesting parameter.

BRIEF DESCRIPTION OF THE DRAWINGS

Below is a detailed description of the invention according to the enclosed drawings, where.

DESCRIPTION OF THE PREFERRED EMBODIMENTS

Figure 1:
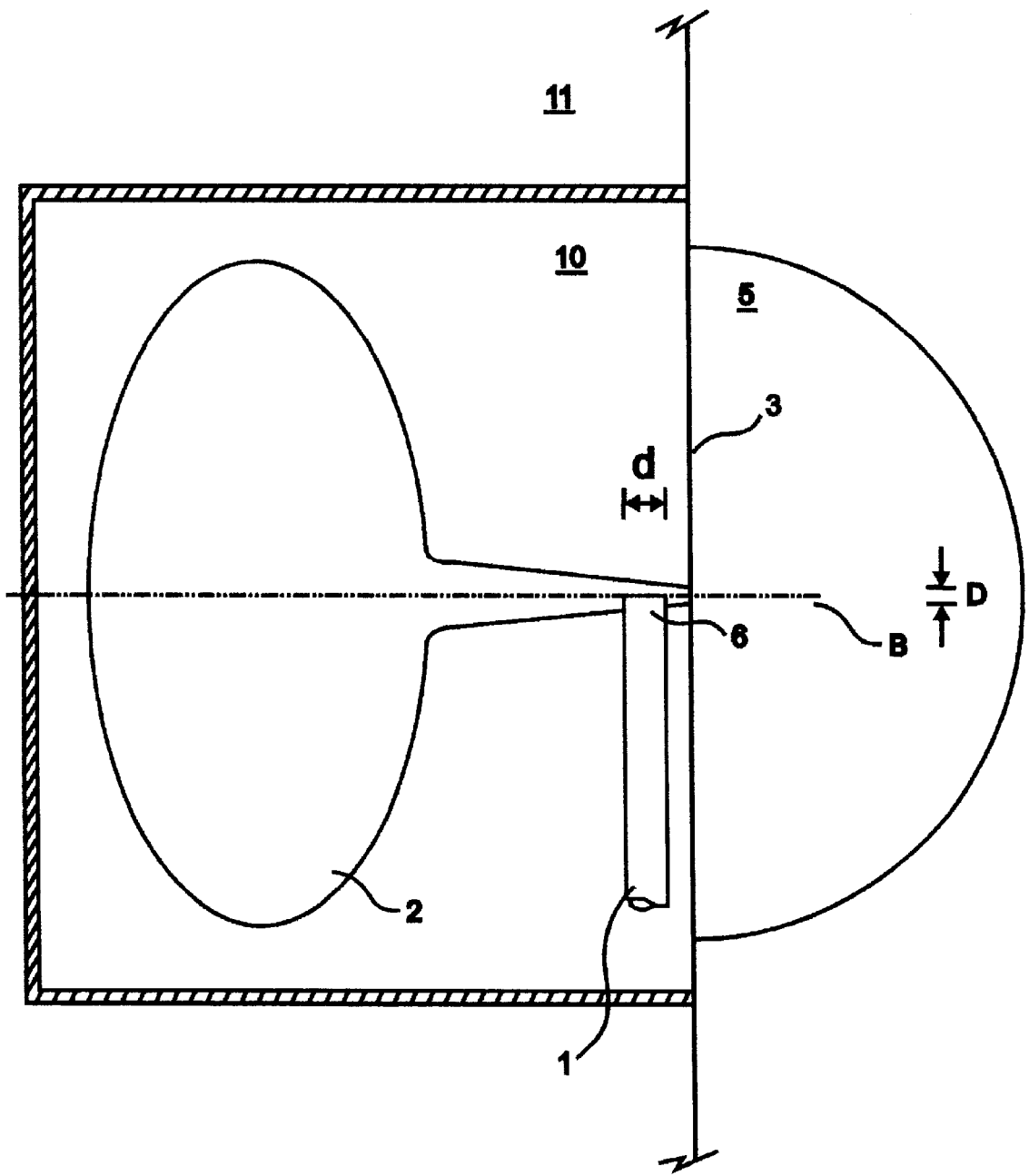
FIG. 1 is a cut-away of a first embodiment of a microsensor according to the invention.

FIG. 1 describes a first embodiment of a microsensor according to the invention. The microsensor has a transducer 1, for example an oxygen microelectrode or a fibre optical sensor. Alternatively, a hydrogen electrode or a nitrous oxide electrode can be used. A reservoir 2 has a passage- or transport area connecting the reservoir and the medium, the passage- or transport area designed as a mouth 3. The transducer 1 has a sensoric tip 6 in the mouth 3, and the transducer 1 is placed perpendicular to the longitudinal axis B of the passage or transport area.

The transducer 1 is placed in an enclosure 10 that surrounds the transducer and the reservoir. The enclosure 10 is inserted in a wall 11 which could be the side wall of a tank or a pipeline containing the medium where the measurement is to take place. The enclosure 10 may be produced of different materials, for example glass or metal or other diffusion-proof material. The reservoir 2 contains a gas or liquid-dissolved substance intended for the diffusion through the mouth 3 into an area 5 outside the mouth 3.

As described, the transducer 1 has a sensoric tip 6 where a partial pressure of the gas in the mouth 3 or a concentration of the dissolved substance in the mouth 3 is being measured.

In the shown embodiment the diameter d of the tip 6 is 2 $\mu$m, and a diameter D of the mouth 3 is 10 $\mu$m.

The area 5 outside the mouth 3 of reservoir 2, into which the gas or the liquid-dissolved substance contained in the reservoir 2 is to diffuse, will in stagnated media be spherical as illustrated. The geometry of the area 5, however, depends on the kind of medium and on the diffusivity and flow conditions in the medium, into which the gas or the dissolved substance diffuses.

The reservoir 2 could contain a liquid with dissolved non-ionized combinations or a gas. Gas contained in the reservoir 2 is mainly hydrogen ($H_2$), carbon monooxide (CO), oxygen ($O_2$) or nitrous oxide ($N_2O$). Applied as tracer, hydrogen ($H_2$) is the preferred gas, because it only appears in modest quantities in the media which flow has to be determined. Oxygen on the contrary, is frequently present in the media and can interfere with the measurements of the transducer.

Figure 2:
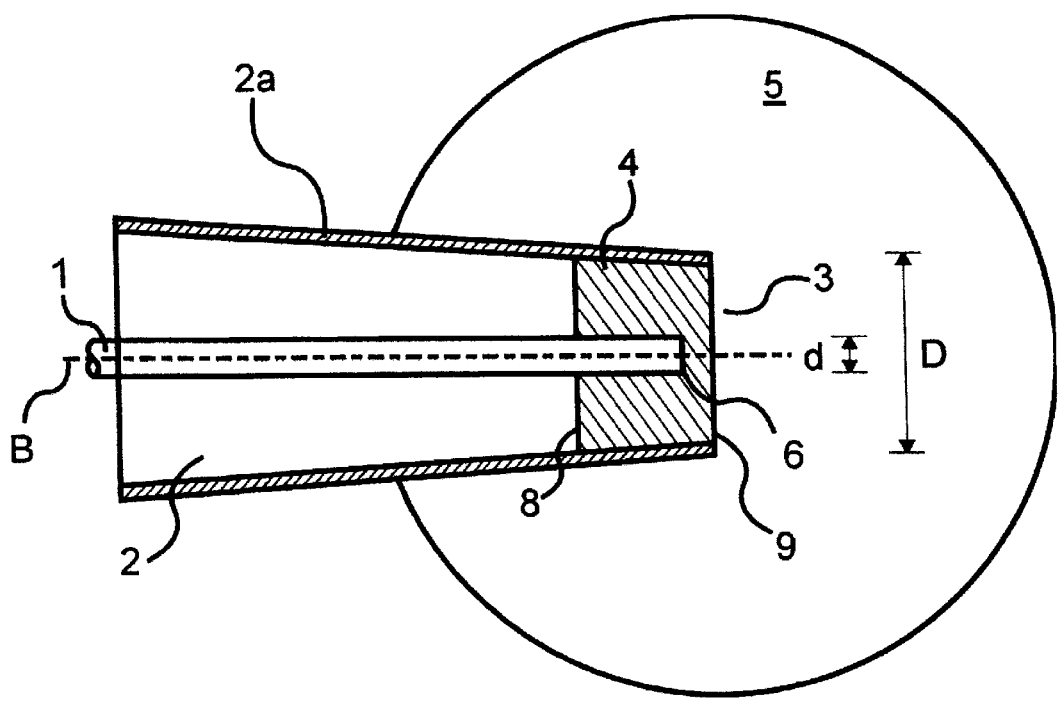
FIG. 2 is a cut-away of a second embodiment of a microsensor according to the invention

FIG. 2 illustrates a second embodiment of a front part of a microsensor according to the invention. The microsensor comprises a transducer 1, for example an oxygen microelectrode or a fibre optical sensor. Alternatively a hydrogen electrode, a carbon monooxide electrode or a nitrous oxide electrode can be used. A reservoir confined by a container 2$a$ has a mouth 3. In the mouth a permeable membrane or insert 4 is placed. The transducer 1 has a tip 6 inserted in the mouth 3, and the transducer is placed with its longitudinal axis parallel with the longitudinal axis B through the microsensor.

The reservoir 2 enclosed by the container 2$a$ surrounds the transducer 1. The permeable membrane or insert 4 in the mouth 3 is in sealing contact with the container 2$a$. The container is made of a material that is not permeable for gasses, for example a metallic material or glass. The membrane or insert 4 is made of silicone. The reservoir 2 contains a gas or a dissolved substance intended for diffusion out through the membrane or insert 4 to an area 5 outside the mouth 3 of the container 2$a$.

As mentioned, in a stagnant medium there will be a spherical diffusion field around the outside of the mouth 3, with decreasing concentrations with increasing distance to the orifice. Spherical diffusion comes to a steady state, and after a short time the concentration field around the mouth of the microsensor will not change, i.e. the transducer 1 placed in the membrane or insert 4 reads a constant concentration. If a flow is imposed in the media 5, the diffusion field will be disturbed as advection will now contribute to the transport of molecules away from the mouth, i.e. the concentration in and outside the membrane 4 will decrease. The higher the flow, the lower the concentration will be in the membrane, where it is sensed by the built-in transducer. The average diffusion time of a gas molecule through a 20 $\mu$m thick membrane is about 0.05 s, so the response to changes in flow rate has about the same time constant with a 90% response below 1 s. The response time will increase with the diameter of the sensor and will be largest at low flows, where the diffusion sphere around the sensor is wide.

As described the transducer 1 has a sensoric tip 6 where the partial pressure or pressure gradient of the gas in the mouth 3 or alternatively the concentration or its gradient of the dissolved substance in the mouth 3 is being measured. Preferably, the measurement of partial pressure or concentration is carried out on tracer material, which has not yet been led into the external medium. As seen on FIG. 2, the transducer 1 measures at the end of the mouth 3, just before the tracer enters the outer field 5. From prior art it is known to add a tracer to a flowing medium, and to place the measuring device or transducer directly in the flowing media, exposed to mechanical influences, surface growth and possible interference on the output signal by outside elements. Instead, measuring inside the passage and placing the transducer in an insert gives a controlled and well defined measuring environment. The insert 4 defines a confined chamber or volume (8,9,A,D) which influences upon the diffusivity of the tracer. The silicone insert impedes the diffusivity, and results in linear curves representing the partial pressure or the concentration. In the shown embodiment an axial length A of the membrane or insert 4 is 10 μm. A diameter d of the tip 6 of the transducer is 2 μm, and a diameter D of the mouth 3 is 10 μm. By enlarging the distance A thereby lengthening the insert, a comparatively larger part of the curve profile is inside the microsensor, which is relevant when measuring small changes in diffusivity. To enhance the sensitivity of measurement, the transducer 1 can be placed outside the membrane or insert 4. However, this means loss of the linear pressure or concentration profile. Also, the insert can be moved and e.g. be placed in the middle of the container 2a between reservoir and mouth 3.

The area 5 outside the mouth 3 of container 2a, into which the gas or the liquid-dissolved substance contained in the reservoir 2 is to diffuse, is in stagnated media spherical as mentioned. The geometry of the area 5, however, depends on the kind of medium or the diffusivity and flow conditions in the medium, into which the gas or the dissolved substance diffuses.

Gas contained in the container 2a is mainly hydrogen ($H_2$), carbon monooxide (CO), oxygen ($O_2$) or nitrous oxide ($N_2O$). The reservoir 2 can also contain a liquid with dissolved non-ionized combinations.

Figure 3:
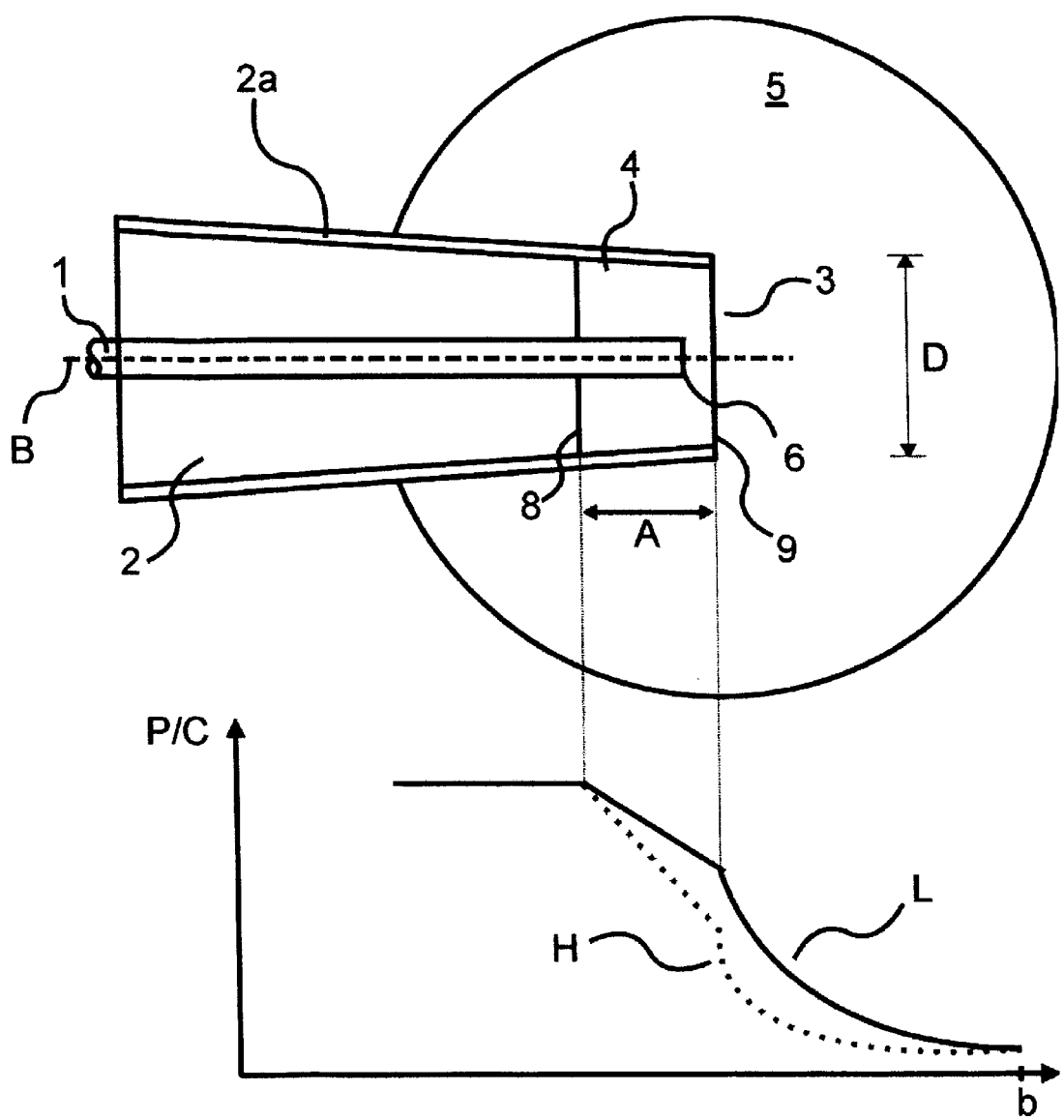
FIG. 3 is a schematic illustration of a measurement of low and high flow velocity

FIG. 3 illustrates curves for a partial pressure of the gas or the concentration of the liquid-dissolved substance contained in the reservoir 2, which diffuses through the membrane or insert 4 into the area 5 of the medium outside the mouth 3. The partial pressure or the concentration is illustrated as a function of the position in the microsensor as illustrated by the longitudinal axis B. The first curve L illustrates the partial pressure or the concentration at diffusion out into a medium with a low flow velocity. The second curve H illustrates the partial pressure or the concentration at diffusion out into a medium with a higher flow velocity. It appears that the partial pressure of the gas or the concentration of the dissolved substance is being reduced as soon as the gas or the dissolved substance begins to diffuse through the membrane or insert 4 from the back 8 to the front 9 of the membrane or insert 4. In other words, the diffusivity or flow velocity is imaged by the concentration or pressure curves. In particular, by measuring in only one point on the curve as shown with the transducer 1, the gradient of the curve can be determined either by means of a look up table or by a simple calculation based on the knowledge of the start pressure or concentration in the reservoir.

In a medium with high flow velocity the partial pressure or concentration will decrease with a numerically large constant gradient from the back 8 of the membrane or insert 4 on to the front 9. From the front 9 the partial pressure or the concentration will decrease with a continuous non-constant gradient. In the start the gradient is numerically larger than the gradient in the membrane or insert 4 but will decrease until a distance b is reached, where the gradient is almost zero.

In a medium with low flow velocity the partial pressure or the concentration decreases with a numerically small constant gradient from the back 8 to the front 9. From the front 9 the partial pressure or concentration decreases with a continously non-constant gradient. In the beginning, the gradient is numerically larger than the gradient in membrane, but decreases until a distance b is reached, where the gradient is almost zero.

Figure 4:
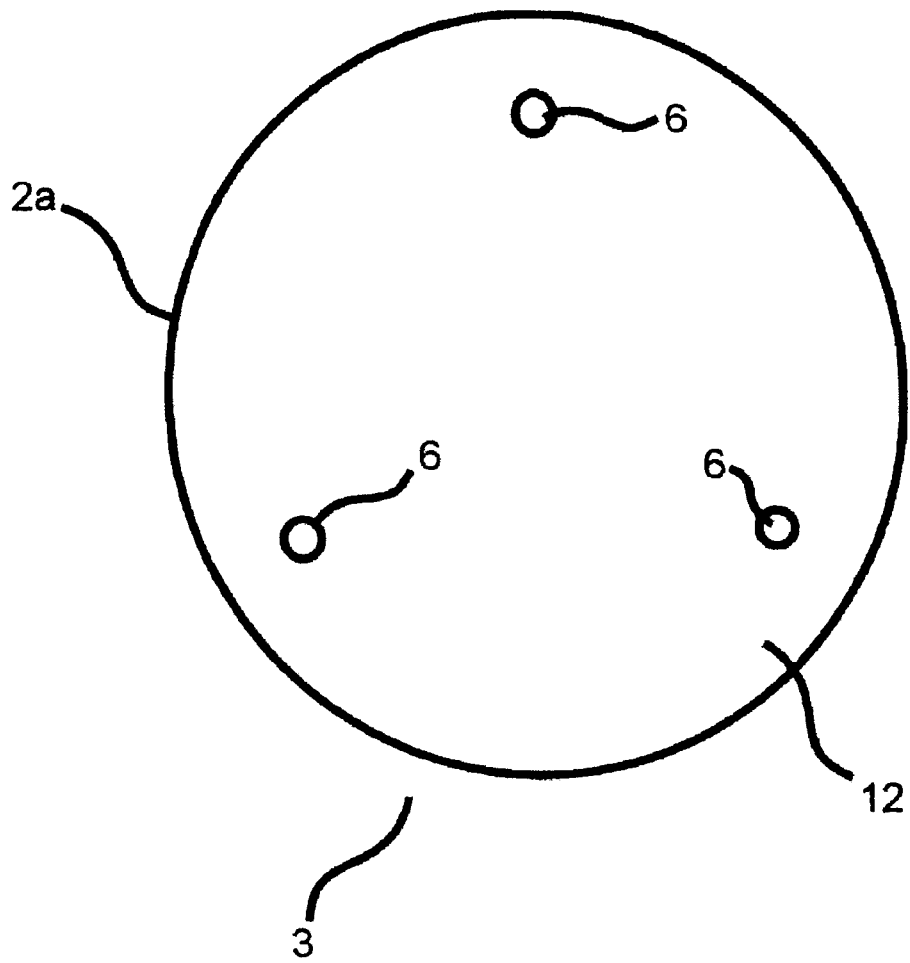
FIG. 4 is an illustration of an embodiment of a mouth in a microsensor according to the invention

FIG. 4 illustrates an embodiment of the mouth 3 in a reservoir 2 and a container 2a. The mouth is shown from a front 12 and has preferably a circular sectional view. In the figure, only the tip 6 of three transducers 1 is shown. Using three or more flow sensors allows a spatial measurement, which can determine the direction of flow. One of the transducers (1) with mouth 6 could be a flow sensor as described herein, which releases a tracer to be detected by the other transducers for determining the flow direction. Different geometries of placing the transducer tips are possible; for example, a flow sensor according to the invention could be placed in the center and surrounded circularly by a number of n tracer transducers, where the number n determines the resolution of the measurement.

Diffusivity and flow velocity can be measured by means of different types of transducers and with mixed gasses or liquid dissolved substances contained in the reservoir 2. For example, a first transducer can be used for the measurement of diffusivity and a second transducer for the measurement of flow velocity, with both transducers placed in the mouth 3.

Furthermore, a set of different types of transducers can be inserted in the mouth 3 for the measurement of diffusivity or flow velocity and also measurement of temperature with a thermosensor. Alternatively, instead of the mouth 3 having a circular sectional view, a mouth with slots can be provided, as known from the art for measurement of shear stress.

Figure 5:
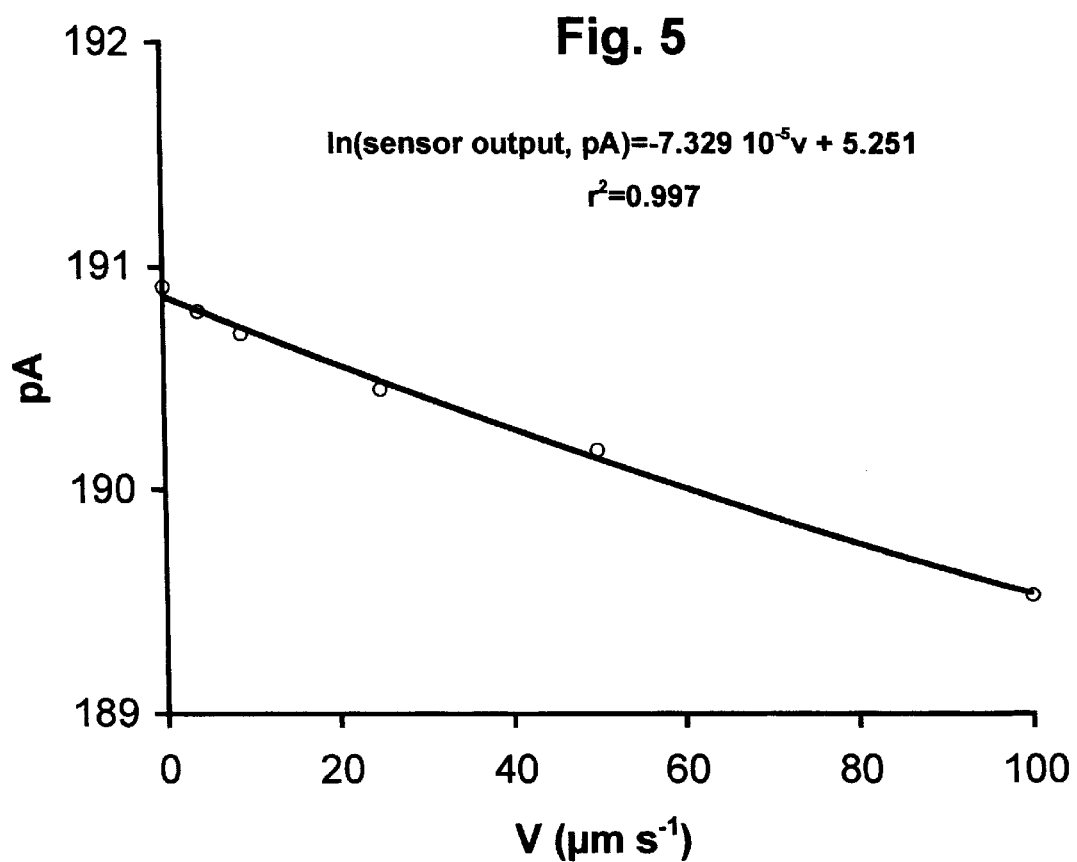
FIG. 5 is a graphical illustration of a calibration process for the microsensor according to the invention.

FIG. 5 is a curve illustrating the calibration of a microsensor according to the invention. The calibration is done for a flow velocity of between 0 μm/s and 100 μm/s. It appears that the sensor output generally decreases linearly in proportion to the flow velocity. The mathematical function followed by the calibration curve is shown above the curve.

Figure 6:
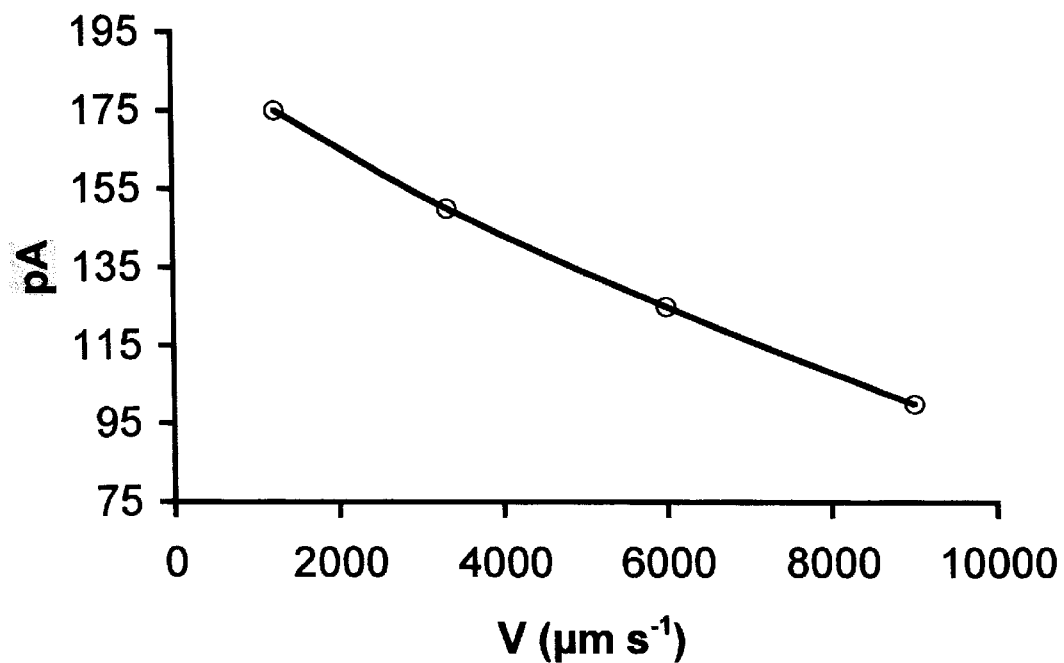
FIG. 6 is a graphical illustration of an estimated measuring range with the microsensor according to the invention.

FIG. 6 illustrates a calculated velocity-current curve of a speed range from 0 mm/s to more than 10 mm/s. The curve is calculated on the basis of the formula shown above the curve. The output of the microsensor decreases exponentially with the flow velocity, but exhibits a close to linear profile at low velocities below 2,5 mm/s.

This invention is described according to specific embodiments. It will, however, be possible to carry out the invention with other design relations between the transducer, the reservoir and possibly the membrane or insert. The embodiment shown in FIG. 1 as well as the one shown in FIG. 2 are available with or without membrane or insert. Other kinds of material than those mentioned can be used for the production of microsensors, the transducer for example can be a fibre optical sensor. More than one transducer or several types of transducers can be used as the measuring device, as well as gas or liquid-dissolved substances or compounds as tracer material. To compensate for temperature differences or temperature gradients the microsensor can also be equipped with a thermo-transducer.

What is claimed is:

1. Method for the measurement of kinetic transport coefficients such as diffusivity or flow velocity in a medium formed by a gas, a liquid or a matrix, comprising the steps of providing a tracer in a gaseous, liquid or liquid dissolved form, locating the tracer in a reservoir, providing a measuring device to measure the tracer as the tracer is emitted from the reservoir into the medium, and measuring the concentration or the partial pressure of the tracer in a passage or transport area having a form of a channel having a mouth and which channel connects the reservoir and the medium, whereby the measurement is carried out on the tracer in the passage or transport area.

2. Method according to claim 1 in which the measuring device determines a curve profile in the form of a gradient of a curve, the curve relating to the partial pressure or the concentration of the tracer in the passage or transport area.

3. Method according to claim 2 in which the measuring device measures the partial pressure or the concentration at only one point in the passage or transport area and the measured value is converted to a gradient of the partial pressure or the concentration.

4. Method according to claim 3 in which the partial pressure or the concentration measured at only one point is compared to known data in an existing data-base to provide information of a relationship between the one point measured partial pressure or concentration and the gradient of the partial pressure or the concentration.

5. Method according to claim 1 in which the passage or transport area contains a device, which influences the diffusivity of the tracer, said device defining a confinement or volume in which the concentration or the partial pressure of the tracer is measured by the measuring device.

6. Microsensor for measuring kinetic transport coefficients such as diffusivity or flow velocity in a medium formed by a gas, a liquid or a matrix, said microsensor comprising a measuring device and a reservoir containing a gas or a substance dissolved as a tracer in a liquid, the measuring device having a sensoric tip located in a passage or transport area comprising a channel having a mouth which, channel connects the reservoir and the medium, the sensoric tip being located close to the mouth of the channel.

7. Microsensor according to claim 6 in which the reservoir surrounds the transducer or measuring device, said reservoir containing a gas or a liquid dissolved substance intended for the diffusion from the reservoir through the channel to a field or an area outside the microsensor.

8. Microsensor according to claim 6, including a membrane or insert open for diffusion of a tracer located in sealing contact with the channel, and the tip of the transducer or measuring device is placed in the membrane or insert.

9. Microsensor according to claim 6 in which the tip of the transducer is located in the mouth of the passage or transport area, and the transducer has a longitudinal axis which is parallel to the longitudinal axis of the passage or transport area.

10. Microsensor according to claim 6 in which the tip of the transducer is located in the mouth of the passage or transport area, and the longitudinal axis of the transducer has a longitudinal axis which is perpendicular to the axis of the passage or transport area.

11. Microsensor according to claim 6, in which the mouth of the reservoir has a size of 2 um and 500 um.

12. Microsensor according to claim 6, in which the reservoir contains at least one gas selected from the group consisting of: nitrous oxide ($N_2O$), oxygen ($O_2$), carbon monoxide (CO) and hydrogen ($H_2$), and the membrane or insert is gas permeable.

13. Microsensor according to claim 6, in which the reservoir contains a liquid with at least one non-ionized dissolved substance, and the membrane or insert is permeable for non-ionized substances.

14. Microsensor according to claim 6, in which the tips of at least two transducers are located in the mouth of the passage or transport area.

15. Method for measuring diffusivity or flow velocity, comprising the steps of using a sensor with a mouth having at least one transducer with the sensor being located in an area or a volume of a medium, extending the medium into a field stretching from the mouth, diffusing a gas or a liquid dissolved material into the medium in the field, determining diffusivity or flow velocity by measuring a partial pressure gradient or a concentration gradient of the gas or the liquid dissolved material, and conducting the measurement in the mouth of the sensor by the transducer.

16. Microsensor for the measurement of diffusivity or flow velocity, comprising a reservoir having a mouth opening to an outside area or volume and at least one transducer, the transducer having a tip and the reservoir surrounding the transducer, the transducer tip being located in the mouth, and the reservoir containing a gas or a liquid dissolved substance determined the diffusion from the reservoir through the mouth to the area or volume outside the mouth.

* * * * *